(12) United States Patent
Terrill (10) Patent No.: US 11,752,000 B2
(45) Date of Patent: Sep. 12, 2023

(54) GLENOID IMPLANT WITH ADDITIVELY MANUFACTURED FIXATION POSTS

(71) Applicant: Howmedica Osteonics Corp., Mahwah, NJ (US)

(72) Inventor: Lance N. Terrill, League City, TX (US)

(73) Assignee: Howmedica Osteonics Corp., Mahwah, NJ (US)

( * ) Notice: Subject to any disclaimer, the term of this patent is extended or adjusted under 35 U.S.C. 154(b) by 42 days.

(21) Appl. No.: 17/180,942

(22) Filed: Feb. 22, 2021

(65) Prior Publication Data

US 2021/0275314 A1 Sep. 9, 2021

Related U.S. Application Data

(60) Provisional application No. 62/984,336, filed on Mar. 3, 2020.

(51) Int. Cl.
*A61F 2/40* (2006.01)
*A61F 2/30* (2006.01)

(52) U.S. Cl.
CPC ........ *A61F 2/4081* (2013.01); *A61F 2/30942* (2013.01); *A61F 2002/30405* (2013.01);
(Continued)

(58) Field of Classification Search
CPC .............. A61F 2/4081; A61F 2/30942; A61F 2002/30405; A61F 2002/30451;
(Continued)

(56) References Cited

U.S. PATENT DOCUMENTS

| 3,559,514 A | 2/1971 | Brownfield |
| 3,803,641 A | 4/1974 | Golyakhovsky |

(Continued)

FOREIGN PATENT DOCUMENTS

| EP | 2853242 A1 | 4/2015 |
| EP | 3403617 A1 | 11/2018 |

(Continued)

OTHER PUBLICATIONS

European Search Report for EP21160317 dated Jul. 2, 2021; 2 pages.

(Continued)

*Primary Examiner* — Brian A Dukert
(74) *Attorney, Agent, or Firm* — Lerner David LLP (57) ABSTRACT

A glenoid implant system may include a main body formed of a polymer, a base, and an anchor formed of metal. The main body may define an articulating surface and an opposite bone-contacting surface. The base may be formed in the bone-contacting surface of the main body, the base including a hole formed therein. The anchor may have a main section and a threaded post extending from the main section. The anchor may include a plurality of ribs extending in a longitudinal direction of the main section, the plurality of ribs being spaced apart from one another in a circumferential direction of the main section. The anchor may further include a plurality of wedges disposed on a base of the anchor, the plurality of wedges adapted to contact the base formed in the bone-contacting surface of the main body when the threaded post is received within the threaded hole.

20 Claims, 5 Drawing Sheets

(52) U.S. Cl.
CPC .............. *A61F 2002/30451* (2013.01); *A61F 2002/30957* (2013.01); *A61F 2002/4085* (2013.01)

(58) Field of Classification Search
CPC .... A61F 2002/30957; A61F 2002/4085; A61F 2002/30004; A61F 2002/30011; A61F 2002/3021; A61F 2002/30317; A61F 2002/30362; A61F 2002/30364; A61F 2002/30367; A61F 2002/30476; A61F 2002/30485; A61F 2002/30515; A61F 2002/30528; A61F 2002/30604; A61F 2002/30736; A61F 2002/30878; A61F 2002/30879; A61F 2002/30884; A61F 2002/30891; A61F 2002/30899; A61F 2002/30901; A61F 2002/30985; A61F 2310/00023; A61F 2/30734
See application file for complete search history.

(56) References Cited

U.S. PATENT DOCUMENTS

| | | | |
|---|---|---|---|
| 3,916,451 A | 11/1975 | Buechel et al. | |
| 3,979,778 A | 9/1976 | Stroot | |
| 4,042,980 A | 8/1977 | Swanson et al. | |
| 4,045,825 A | 9/1977 | Stroot | |
| 4,045,826 A | 9/1977 | Stroot | |
| 4,206,517 A | 6/1980 | Pappas et al. | |
| 4,355,429 A | 10/1982 | Mittelmeier et al. | |
| 4,550,450 A | 11/1985 | Kinnett | |
| D285,968 S | 9/1986 | Kinnett | |
| 4,725,280 A | 2/1988 | Laure | |
| D295,076 S | 4/1988 | Homsy et al. | |
| 4,865,605 A | 9/1989 | Dines et al. | |
| 4,919,669 A | 4/1990 | Lannelongue | |
| 4,964,865 A | 10/1990 | Burkhead et al. | |
| 4,964,867 A | 10/1990 | Boger | |
| 4,986,833 A | 1/1991 | Worland | |
| 5,030,219 A | 7/1991 | Matsen, III et al. | |
| 5,032,132 A | 7/1991 | Matsen, III et al. | |
| 5,080,673 A | 1/1992 | Burkhead et al. | |
| 5,108,446 A | 4/1992 | Wagner et al. | |
| 5,203,653 A | 4/1993 | Kudla | |
| 5,360,452 A | 11/1994 | Engelhardt et al. | |
| 5,437,677 A | 8/1995 | Shearer et al. | |
| 5,489,309 A | 2/1996 | Lackey et al. | |
| 5,489,310 A | 2/1996 | Mikhail | |
| 5,512,145 A | 4/1996 | Hollenberg | |
| 5,549,691 A | 8/1996 | Harwin | |
| 5,591,170 A | 1/1997 | Spievack et al. | |
| 5,593,448 A | 1/1997 | Dong | |
| 5,702,447 A | 12/1997 | Walch et al. | |
| 5,800,551 A | 9/1998 | Williamson et al. | |
| 5,919,195 A | 7/1999 | Wilson et al. | |
| 6,102,951 A | 8/2000 | Sutter et al. | |
| 6,228,119 B1 | 5/2001 | Ondrla et al. | |
| 6,245,074 B1 | 6/2001 | Allard et al. | |
| 6,277,390 B1 | 8/2001 | Schaffner | |
| 6,364,910 B1 | 4/2002 | Shultz et al. | |
| 6,379,386 B1 | 4/2002 | Resch et al. | |
| 6,406,495 B1 * | 6/2002 | Schoch ................ | A61F 2/4081 623/19.13 |
| 6,448,315 B1 | 9/2002 | Lidgren et al. | |
| 6,506,214 B1 | 1/2003 | Gross | |
| 6,506,216 B1 | 1/2003 | McCue et al. | |
| 6,514,287 B2 | 2/2003 | Ondrla et al. | |
| 6,673,115 B2 | 1/2004 | Resch et al. | |
| 6,699,289 B2 | 3/2004 | Iannotti et al. | |
| 6,761,740 B2 | 7/2004 | Tornier | |
| 6,875,234 B2 | 4/2005 | Lipman et al. | |
| 6,911,047 B2 | 6/2005 | Rockwood, Jr. et al. | |
| 6,949,101 B2 | 9/2005 | McCleary et al. | |
| 7,217,271 B2 | 5/2007 | Wolford et al. | |
| 7,473,254 B2 | 1/2009 | White et al. | |
| 7,503,921 B2 | 3/2009 | Berthusen et al. | |
| 7,572,259 B2 | 8/2009 | Desarzens et al. | |
| 7,637,909 B2 | 12/2009 | Lechot et al. | |
| 7,749,227 B2 | 7/2010 | Lechot et al. | |
| 7,753,959 B2 | 7/2010 | Berelsman et al. | |
| 7,780,669 B2 | 8/2010 | Lechot et al. | |
| 7,785,329 B2 | 8/2010 | Lechot et al. | |
| 7,803,160 B2 | 9/2010 | Keller | |
| 7,819,875 B2 | 10/2010 | Chana | |
| 7,892,287 B2 | 2/2011 | Deffenbaugh | |
| 7,922,769 B2 | 4/2011 | Deffenbaugh et al. | |
| 7,927,335 B2 | 4/2011 | Deffenbaugh et al. | |
| 3,052,690 A1 | 11/2011 | Berthusen et al. | |
| 8,231,683 B2 | 7/2012 | Lappin et al. | |
| 8,241,365 B2 | 8/2012 | Williams, Jr. et al. | |
| 8,282,639 B2 | 10/2012 | Chana | |
| 8,425,614 B2 | 4/2013 | Winslow et al. | |
| 8,449,617 B1 | 5/2013 | McDaniel et al. | |
| 8,465,548 B2 | 6/2013 | Long | |
| 8,475,460 B1 | 7/2013 | Roger et al. | |
| 8,480,674 B1 | 7/2013 | Roger et al. | |
| 8,480,750 B2 | 7/2013 | Long | |
| 8,486,076 B2 | 7/2013 | Chavarria et al. | |
| 8,506,638 B2 | 8/2013 | Vanasse et al. | |
| 8,556,980 B2 | 10/2013 | Deffenbaugh | |
| 8,632,598 B2 | 1/2014 | McDaniel et al. | |
| 8,657,833 B2 | 2/2014 | Burgi et al. | |
| 8,657,834 B2 | 2/2014 | Burgi | |
| 8,721,727 B2 | 5/2014 | Ratron et al. | |
| 8,740,907 B2 | 6/2014 | Penenberg | |
| 8,771,275 B2 | 7/2014 | Xie et al. | |
| 8,858,641 B2 | 10/2014 | Viscardi et al. | |
| 8,864,834 B2 | 10/2014 | Boileau et al. | |
| 8,870,962 B2 | 10/2014 | Roche et al. | |
| 8,876,907 B2 | 11/2014 | Baptista et al. | |
| 8,876,908 B2 | 11/2014 | Katrana et al. | |
| 8,906,102 B2 | 12/2014 | Viscardi et al. | |
| 8,920,508 B2 | 12/2014 | Iannotti et al. | |
| 8,961,611 B2 | 2/2015 | Long | |
| D730,522 S | 5/2015 | Goldberg | |
| 9,066,730 B2 | 6/2015 | McMinn et al. | |
| 9,066,731 B2 | 6/2015 | Moore | |
| 9,078,672 B1 | 7/2015 | Rosse | |
| 9,089,348 B2 | 7/2015 | Chavarria et al. | |
| 9,149,362 B2 | 10/2015 | Deffenbaugh et al. | |
| 9,161,843 B2 | 10/2015 | Deffenbaugh et al. | |
| 9,233,003 B2 | 1/2016 | Roche et al. | |
| 9,301,848 B2 | 4/2016 | Long | |
| 9,320,527 B2 | 4/2016 | Kehres et al. | |
| 9,320,619 B2 | 4/2016 | Anthony et al. | |
| 9,326,865 B2 | 5/2016 | Katrana et al. | |
| 9,345,582 B2 | 5/2016 | Bickley et al. | |
| D759,819 S | 6/2016 | Goldberg | |
| 9,364,334 B2 | 6/2016 | Katrana et al. | |
| 9,408,652 B2 | 8/2016 | Hassler et al. | |
| 9,414,927 B2 | 8/2016 | Iannotti et al. | |
| 9,421,106 B2 | 8/2016 | Splieth et al. | |
| 9,439,768 B2 | 9/2016 | Iannotti et al. | |
| 9,498,345 B2 | 11/2016 | Burkhead, Jr. et al. | |
| 9,545,312 B2 | 1/2017 | Tornier et al. | |
| 9,585,769 B2 | 3/2017 | Lubensky et al. | |
| 9,629,725 B2 | 4/2017 | Gargac et al. | |
| 9,636,237 B2 | 5/2017 | Lubensky et al. | |
| 9,681,960 B2 | 6/2017 | Olson et al. | |
| 9,693,880 B2 | 7/2017 | Anthony et al. | |
| 9,700,436 B2 | 7/2017 | Anthony et al. | |
| 9,700,437 B2 | 7/2017 | Anthony et al. | |
| 9,713,540 B2 | 7/2017 | Anthony et al. | |
| 9,775,716 B2 | 10/2017 | Goldberg | |
| 9,788,957 B2 | 10/2017 | Koka | |
| 9,814,471 B2 | 11/2017 | Goldberg et al. | |
| 9,814,588 B2 | 11/2017 | Goldberg | |
| 9,861,376 B2 | 1/2018 | Chavarria et al. | |
| D810,940 S | 2/2018 | Goldberg | |
| 9,943,318 B2 | 4/2018 | Anthony et al. | |
| 9,943,419 B2 | 4/2018 | Anthony et al. | |
| 10,028,838 B2 * | 7/2018 | Hodorek ................ | A61B 17/17 |
| 10,034,757 B2 | 7/2018 | Kovacs et al. | |
| 10,034,777 B2 | 7/2018 | Kovacs et al. | |

(56) References Cited

U.S. PATENT DOCUMENTS

| | | |
|---|---|---|
| 10,064,734 B2 | 9/2018 | Burkhead, Jr. et al. |
| 10,085,856 B2 | 10/2018 | Anthony et al. |
| 10,130,480 B2 | 11/2018 | Masini et al. |
| D835,276 S | 12/2018 | Humphrey |
| 10,159,500 B2 | 12/2018 | Chavarria et al. |
| 10,357,373 B2 | 7/2019 | Gargac et al. |
| 10,390,972 B2 | 8/2019 | Rao |
| 10,433,969 B2 | 10/2019 | Humphrey |
| 10,449,054 B2 | 10/2019 | Hopkins |
| 10,485,556 B2 | 11/2019 | Kehres et al. |
| 10,485,557 B2 | 11/2019 | Kehres et al. |
| 10,524,931 B2 | 1/2020 | Lubensky et al. |
| 2001/0011192 A1 | 8/2001 | Ondrla et al. |
| 2001/0037153 A1 | 11/2001 | Rockwood et al. |
| 2002/0082702 A1 | 6/2002 | Resch et al. |
| 2003/0055507 A1 | 3/2003 | McDevitt et al. |
| 2003/0125809 A1 | 7/2003 | Iannotti et al. |
| 2003/0158605 A1 | 8/2003 | Tornier |
| 2003/0163135 A1 | 8/2003 | Hathaway |
| 2003/0216813 A1 | 11/2003 | Ball et al. |
| 2003/0220646 A1 | 11/2003 | Thelen et al. |
| 2004/0059424 A1 | 3/2004 | Guederian et al. |
| 2004/0097947 A1 | 5/2004 | Wolford et al. |
| 2004/0122519 A1 | 6/2004 | Wiley et al. |
| 2004/0122520 A1 | 6/2004 | Lipman et al. |
| 2004/0193276 A1 | 9/2004 | Maroney et al. |
| 2004/0230197 A1 | 11/2004 | Tornier et al. |
| 2004/0236339 A1 | 11/2004 | Pepper |
| 2005/0049709 A1 | 3/2005 | Tornier |
| 2005/0060039 A1 | 3/2005 | Cyprien |
| 2005/0159751 A1 | 7/2005 | Berthusen et al. |
| 2005/0209700 A1 | 9/2005 | Rockwood et al. |
| 2005/0246028 A1 | 11/2005 | Pappas et al. |
| 2005/0261775 A1 | 11/2005 | Baum et al. |
| 2006/0015110 A1 | 1/2006 | Pepper |
| 2006/0058809 A1 | 3/2006 | Zink et al. |
| 2006/0074430 A1 | 4/2006 | Deffenbaugh et al. |
| 2007/0038302 A1 | 2/2007 | Shultz et al. |
| 2007/0038303 A1 | 2/2007 | Myerson et al. |
| 2007/0093840 A1 | 4/2007 | Pacelli et al. |
| 2007/0162147 A1 | 7/2007 | Lewis et al. |
| 2008/0262624 A1 | 10/2008 | White et al. |
| 2009/0270863 A1 | 10/2009 | Maisonneuve |
| 2010/0228352 A1 | 9/2010 | Courtney, Jr. et al. |
| 2011/0004215 A1 | 1/2011 | Bradley et al. |
| 2011/0035013 A1* | 2/2011 | Winslow ............... A61F 2/4081 623/19.13 |
| 2012/0109229 A1 | 5/2012 | Forsell |
| 2012/0123419 A1 | 5/2012 | Purdy et al. |
| 2012/0239042 A1 | 9/2012 | Lappin et al. |
| 2013/0144393 A1 | 6/2013 | Mutchler et al. |
| 2013/0150975 A1 | 6/2013 | Iannotti et al. |
| 2014/0194995 A1 | 7/2014 | Koka |
| 2014/0257495 A1 | 9/2014 | Goldberg |
| 2015/0094822 A1 | 4/2015 | Vogt |
| 2015/0250602 A1* | 9/2015 | Sikora ............... A61F 2/4081 623/19.12 |
| 2016/0310285 A1 | 10/2016 | Kovacs et al. |
| 2018/0303619 A1 | 10/2018 | Kehres et al. |
| 2020/0309185 A1* | 10/2020 | Hess ............... F16B 39/282 |

FOREIGN PATENT DOCUMENTS

| | | |
|---|---|---|
| WO | 2011149590 A1 | 12/2011 |
| WO | 2015130006 A1 | 9/2015 |
| WO | 2016147163 A1 | 9/2016 |

OTHER PUBLICATIONS

Extended European Search Report including Written Opinion for Application No. EP20185044.3, dated Nov. 17, 2020, pp. 1-6.

Karelse, Anne, et al. "Rocking-horse phenomenon of the glenoid component: the importance of inclination." Journal of Shoulder and Elbow Surgery 24.7 (Mar. 11, 2015): 1142-1148.

Knowles, N. K., Ferreira, L. M., & Athwal, G. S. (Jan. 23, 2016). The arthritic glenoid: anatomy and arthroplasty designs. Current reviews in musculoskeletal medicine, 9(1), 23-29. <https://doi.org/10.1007/s12178-016-9314-2>.

Knowles, Nikolas K et al. "Augmented glenoid component designs for type B2 erosions: a computational comparison by volume of bone removal and quality of remaining bone." Journal of shoulder and elbow surgery vol. 24,8 (Jan. 31, 2015): 1218-26. doi:10.1016/j.jse.2014.12.018.

Knowles, Nikolas K., "Osteoarthritis Induced Glenoid Morphology and Bone Quality: An Evaluation of Augmented Glenoid Components", Apr. 15, 2015, Electronic Thesis and Dissertation Repository. 2752, 172 pages, <https://ir.lib.uwo.ca/etd/2752>.

McGuire, DT, Vrettos, B, Roche, S, & Walters, J. (Jan. 2012). Bone loss in shoulder replacement surgery: a review of current management. SA Orthopaedic Journal, 11(3), 47-55. Retrieved Jul. 9, 2020, from <http://www.scielo.org.za/scielo.php?script=sci_arttext&pid=S1681-150X2012000300005&lng=en&tlng=en>.

* cited by examiner

GLENOID IMPLANT WITH ADDITIVELY MANUFACTURED FIXATION POSTS

CROSS-REFERENCE TO RELATED APPLICATIONS

This application claims the benefit of the filing date of U.S. Provisional Patent Application No. 62/984,336, filed Mar. 3, 2020 and titled "Glenoid Implant with Additively Manufactured Fixation Posts," the disclosure of which is hereby incorporated by reference herein.

BACKGROUND OF THE DISCLOSURE

Eccentric glenoid erosion occurs in as much as 40% of shoulder arthroplasty candidates. Wear can present anteriorly, superiorly and posteriorly, with superior being most common in reverse shoulder arthroplasty ("RSA") candidates, and posterior being most prevalent in total shoulder arthroplasty ("TSA") candidates. As the articular surface of the glenoid wears or degrades over time, the glenoid surface may take a biconcave shape. The worn or degraded portion of the glenoid may be referred to as the neoglenoid and the original portion of the glenoid may be referred to as the paleoglenoid.

As the neoglenoid is developed, it may begin to form a pseudo-articular surface that has cortical-type bone. Glenoid prostheses that are designed to fit the neoglenoid preferably closely approximate the surfaces of both the neoglenoid and the paleoglenoid, in order to transfer stress to the bone in a manner that replicates the pre-operative state. Any glenoid implant that does not have a biconvex design to match the concave surface of a glenoid with eccentric glenoid erosion may also require removal of a relatively large amount of bone stock, including portions of the paleoglenoid, which may be undesirable. As eccentric glenoid erosion progresses, the relative sizes and shapes of the paleoglenoid and the neoglenoid may also change. It would thus be preferable to have an augmented glenoid implant that is capable of being implanted onto a glenoid with eccentric glenoid erosion to minimize the amount of native bone stock that needs to be removed.

Still further, most glenoid prostheses require cement to fix the prosthesis to the native glenoid. In at least some scenarios, it is preferable to fix a glenoid prosthesis to the native glenoid without the use of cement. For such glenoid implants, it may be preferable to form the prosthesis at least partially of a polymeric material to provide reduced stiffness of the implant, and at least partially of metal with ingrowth features to help provide long-term fixation of the glenoid prosthesis to the glenoid. Thus, it would be desirable to have a prosthetic glenoid implant that includes polymeric materials while also including features to enhance fixation of the glenoid prosthesis to the native glenoid.

BRIEF SUMMARY

According to one aspect of the disclosure, a glenoid implant system includes a main body, a base, and an anchor. The main body may be formed of a polymer, the main body defining an articulating surface configured to articulate with a humeral head, and an opposite bone-contacting surface adapted to contact the glenoid of a patient. The base may be formed in the bone-contacting surface of the main body. The base may include a hole (which may be threaded) formed therein. The anchor may have a main section and a threaded post extending from the main section. The anchor may include a plurality of ribs extending in a longitudinal direction of the main section, the plurality of ribs being spaced apart from one another in a circumferential direction of the main section. The anchor may further include an anti-rotation feature, which in some embodiments may be a plurality of wedges, disposed on a base of the anchor. The anti-rotation feature may be adapted to contact the base formed in the bone-contacting surface of the main body when anchor is coupled to the base and/or when the threaded post is received within the hole. The anchor may be at least partially formed of metal, such as titanium, including porous titanium. The polymer may be polyethylene. The system may also include an augment portion positioned on the main body. The augment portion may have a bone-contacting surface having a first convexity adapted to contact a neoglenoid portion of the scapular glenoid, and a second convexity adapted to contact a paleoglenoid portion of the glenoid, the first convexity being different than the second convexity. The augment portion may be formed of metal, such as titanium, including porous titanium. The augment portion may include an augment anchor adapted to engage the neoglenoid portion of the glenoid. The augment anchor may be integral with the augment portion. The anchor may include a center anchor and at least one peripheral anchor, and the base formed in the bone-contacting surface of the main body may include a center base and at least one peripheral base, the center base being positioned in a central area of the bone-contacting surface of the main body. Each of the plurality of wedges may include a first edge extending a first distance from the base of the anchor, and a second edge opposite the first edge extending a second distance from the base of the anchor, the second distance being greater than the first distance. Each of the plurality of wedges may be oriented so that, upon rotation of the anchor (and/or the threaded post) in a first direction to couple the anchor (and/or the threaded post) to the hole, the first edges of the plurality of wedges lead the rotation, and the second edges of the plurality of wedges trail the rotation. The anchor may be coupled to the main body so that when the base of the anchor is in contact with the base formed in the bone-contacting surface of the main body, the plurality of wedges extend a distance into the main body to prevent rotation of the anchor (and/or the threaded post) in a second direction opposite the first direction.

According to another aspect of the disclosure, a method of manufacturing a glenoid implant system may include molding a polymer into a main body of the glenoid implant system, the main body defining an articulating surface configured to articulate with a humeral head, and an opposite bone-contacting surface adapted to contact the glenoid of a patient, a base being formed in the bone-contacting surface of the main body. The method may further include forming a hole in the base of the main body. The method may additionally include forming an anchor from metal via additive manufacturing. The anchor may have a main section. The anchor may also have a threaded post extending from the main section. The anchor may include a plurality of ribs extending in a longitudinal direction of the main section, the plurality of ribs being spaced apart from one another in a circumferential direction of the main section. The anchor may also include an anti-rotation feature, which in some embodiments may be a plurality of wedges, disposed on a base of the anchor. The anti-rotation feature may be adapted to contact the base formed in the bone-contacting surface of the main body when the threaded post is received within the hole. The method my also include coupling the anchor to the base of the main body by threading the threaded post of the anchor into the hole of the base of the main body. Coupling the anchor to the base of the main body may include threading the threaded post of the anchor into the hole of the base of the main body until the base of the anchor contacts the base of the main body, and until the anti-rotation feature digs into the bone-contacting surface of the main body. The method may also include forming an augment portion to include a bone-contacting surface with a first convexity adapted to contact a neoglenoid portion of the humerus. Molding the polymer into the main body may also include forming a second convexity in the bone-contacting surface of the main body, the second convexity being adapted to contact a paleoglenoid portion of the humerus, the first convexity being different than the second convexity. Molding the polymer into the main body portion may include overmolding the main body onto the augment portion. Forming the augment portion may include additively manufacturing the augment portion.

DETAILED DESCRIPTION

When referring to specific directions in the following discussion of certain implantable joint replacement prostheses, it should be understood that such directions are described with regard to the orientation and position of the prosthesis devices during exemplary application to the human body in an intended position and/or orientation. Thus, as used herein, the term "proximal" means situated nearer to the heart of the body and the term "distal" means more situated away from the heart. The term "anterior" means towards the front part of the body or the face and the term "posterior" means towards the back of the body. The term "medial" means toward the midline of the body and the term "lateral" means away from the midline of the body. Further, as used herein, the terms "about," "generally," and "substantially" are intended to mean deviations from absolute are included within the scope of the term so modified.

Figure 1A:
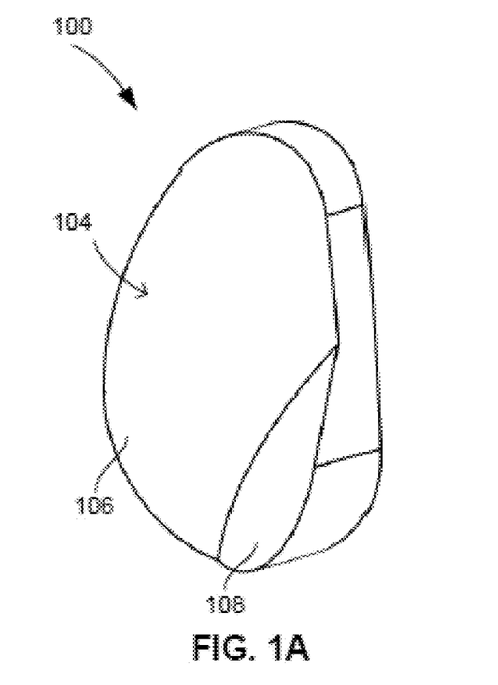
FIGS. 1A and 1B are perspective views of an augmented glenoid implant according to one embodiment of the disclosure.
Figure 1B:
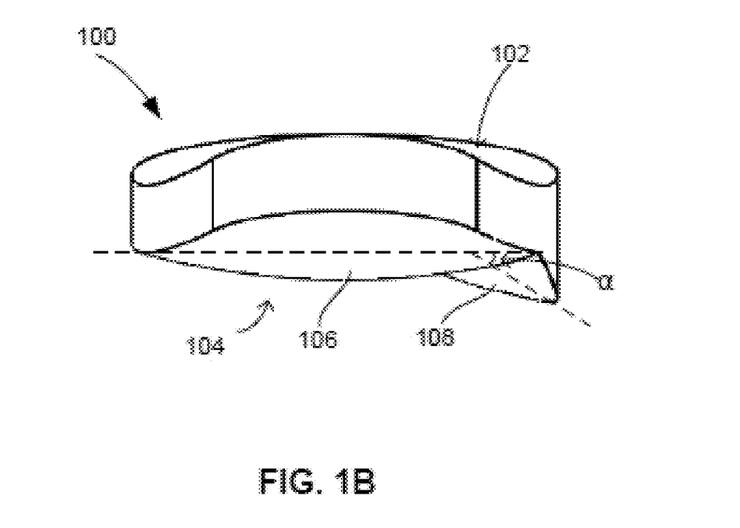
Figure 1C:
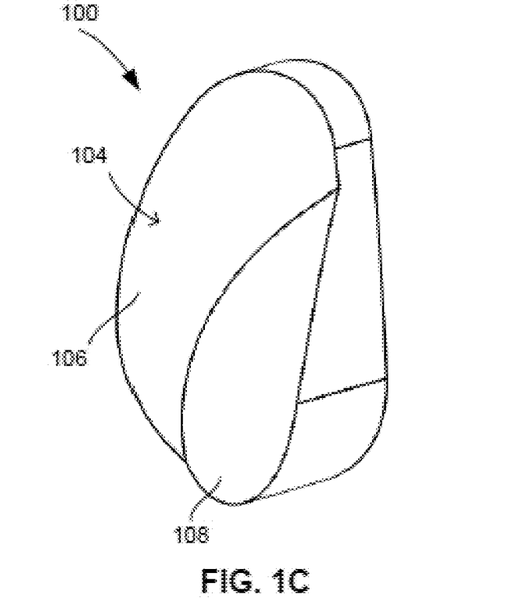
FIGS. 1C and 1D are perspective views of an augmented glenoid implant with an augment different than the augment in FIGS. 1A and 1B.
Figure 1D:
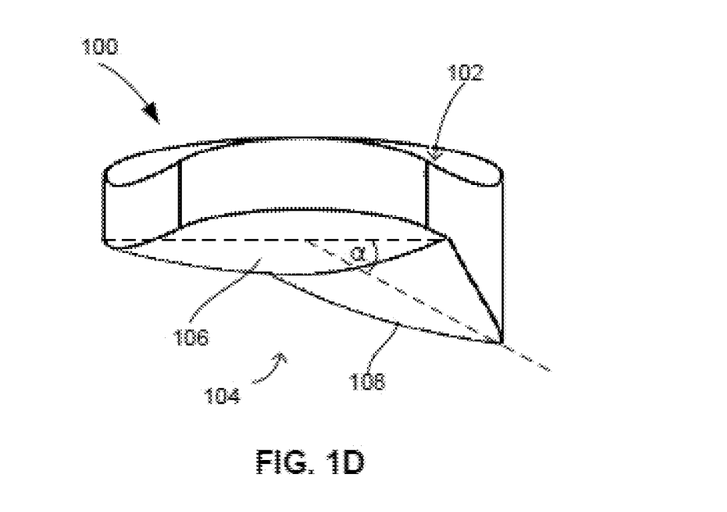
Figure 1E:
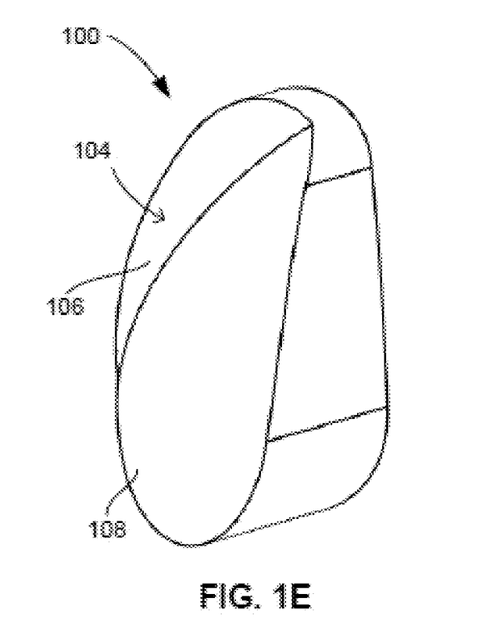
FIGS. 1E and 1F are perspective views of an augmented glenoid implant with an augment different than the augments in FIGS. 1A-1D.
Figure 1F:
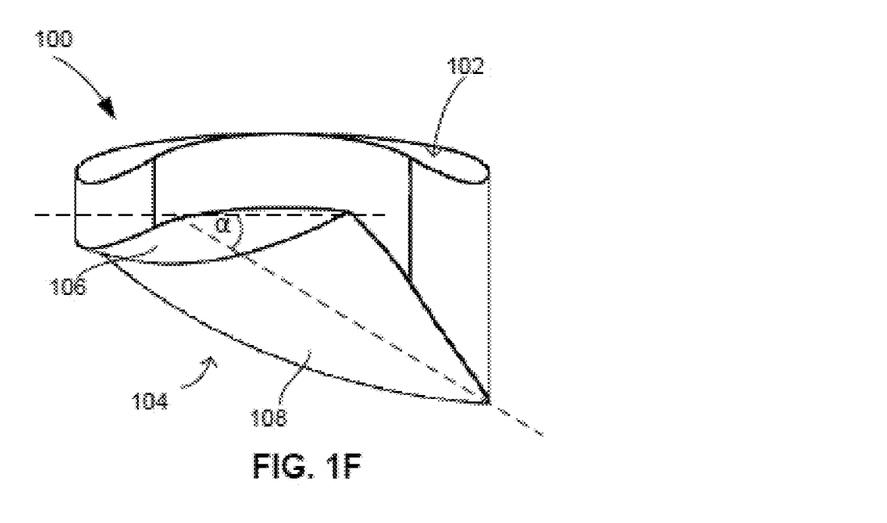

FIGS. 1A-1F depict an exemplary prosthetic glenoid implant for a right shoulder of a patient. It should be understood that a left glenoid implant may be provided that is substantially identical to the right glenoid implants described herein, although the left glenoid implants may be a substantially mirror image to the right glenoid implants described. FIGS. 1A, 1C, 1E depict side perspective views, while FIGS. 1B, 1D, 1F depict corresponding perspective views. Glenoid implant 100 may include a lateral articulating surface 102 and a medial bone-contacting surface 104. The articulating surface 102 is intended for articulating with a corresponding humeral head of the shoulder joint, whether a native or prosthetic humeral head. The bone-contacting surface 104 is intended for being in contact with the patient's glenoid upon implantation. A first portion 106 of the implant 100 is located on a generally anterior portion of implant 100. The first portion 106 has a first convexity sized and shaped to match or substantially match the concavity of the paleoglenoid. A second portion 108 of the implant 100 is located on a generally posterior portion of implant 100. The second portion 108 has a second convexity sized and shaped to match or substantially match the concavity of the neoglenoid. The convexity of the first portion 106 is different from the convexity of the second portion 108.

The different convexities of the first portion 106 and the second portion 108 results in the bone-contacting surface 104 having a biconvex shape. The biconvex shape is configured to better match the degradation of the glenoid in the case of eccentric glenoid degradation that produces a neoglenoid in addition to the paleoglenoid. In such circumstances, the glenoid does not degrade evenly, thereby forming the neoglenoid and the paleoglenoid as noted above. The neoglenoid is the portion that is worn or degraded such that it becomes a secondary-articular surface formed of cortical-type bone. The portion of the glenoid that is not (or is less significantly) degraded or worn is the paleoglenoid. Thus, the biconvexity of the implant 100 allows the implant to have better contact with the eccentrically-worn glenoid upon implantation.

The first portion 106 and the second portion 108 meet or intersect at different locations on implant 100 depending on the degree or severity of degradation found in the native glenoid being replaced. For example, the glenoid implant 100 of FIGS. 1A-B has a relatively small neoglenoid component (or second portion) 108 and a relatively large paleoglenoid component (or first portion) 106 compared to the other embodiments. On the other hand, the glenoid implant 100 of FIGS. 1E-F has a relatively large neoglenoid component (or second portion) 108 and a relatively small paleoglenoid component (or first portion) 106 compared to the other embodiments. Thus, as should be understood, the glenoid implant 100 of FIGS. 1C-D has a neoglenoid component (or second portion) 108 and a paleoglenoid component (or first portion) 106 with a size generally in-between the other two embodiments. The differences in the size and position of the neoglenoid component (or second portion) 108 may generally correspond to an increasing progression in eccentric glenoid degradation, with FIGS. 1A-B corresponding to a relatively early progression of eccentric degradation and FIGS. 1E-F corresponding to a relatively late progression of eccentric degradation. Moreover, the first portion 106 and the second portion 108 meet at an angle transverse from the anterior-posterior axis of the implant 100. In the view of FIGS. 1B, 1D, and 1F, the anterior direction generally corresponds to the left side of the page, while the posterior direction generally corresponds to the right side of the page. In one example, the angle may be about 30 degrees from the anterior-posterior axis such that the first portion 106 and the second portions 108 intersect at a 30 degree posterior bias of the neoglenoid. In some embodiments, the angle may be about 10 degrees below the anterior-posterior axis. However, it should be understood that such angles are merely exemplary, and unless noted otherwise, other angles, including angles of between about 10 degrees and about 30 degrees may be appropriate. While it is described that the first portion 106 and second portion 108 meet at an angle, that angle is descriptive of the direction of the line of intersection. The line of intersection between the first portion 106 and the second portions 108 may be a curved line that follows a typical progression of degradation, which starts posterior to the midline and moves anterior of the midline as the glenoid wears away. Thus, as noted above, FIGS. 1A and 1B depict implant 100 for instances in which there is a relatively small amount of degradation of the glenoid whereas FIGS. 1E, 1F depict implant 100 for instances in which there is a relatively large amount of degradation of the glenoid.

As depicted in FIGS. 1B, 1D, and 1F, the bone-contacting surface 104 of the second portion 108 may be inclined with respect to the bone-contacting surface 104 of the first portion 106. Therefore, the apex of the second portion 108 may extend past the apex of the convex bone-contacting surface 104 of the first portion 106. In some embodiments, the angle of inclination a may be about 15 degrees. However, it should be understood that such an angle is merely exemplary, and unless noted otherwise, other angles, including angles of between about 5 degrees and about 30 degrees may be appropriate.

Figure 2A:
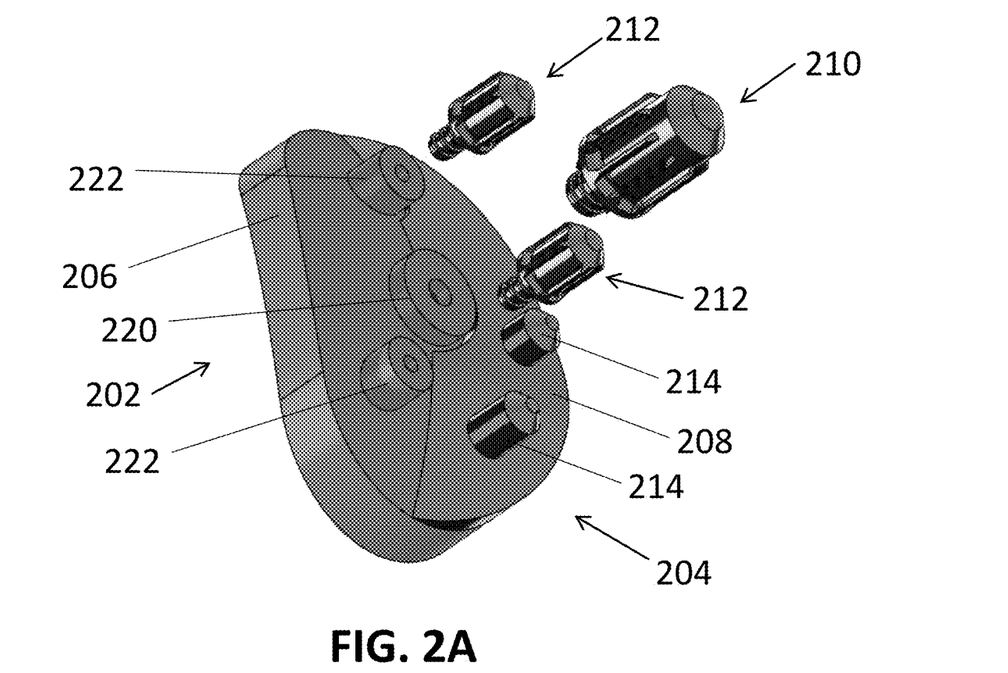
FIGS. 2A-B are perspective views of an augmented implant according to another embodiment of the disclosure.
Figure 2B:
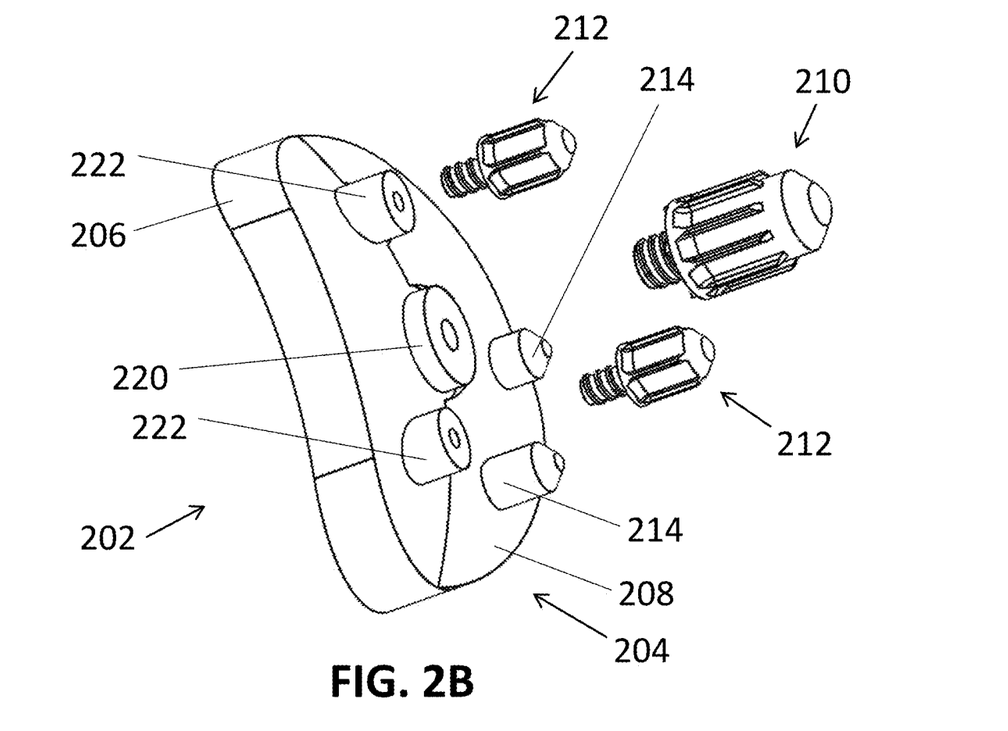

FIGS. 2A-B depict another embodiment of an augmented glenoid implant. Implant 200 has a medial articulating surface 202 and a bone-contacting surface 204. The bone-contacting surface 204 has a biconvex shape and may be comprised of two different portions. The implant 200 may include a main body 206 that defines the entire articulating surface 202, and a portion of the bone-contacting surface 204 having a first convexity and intended to contact the paleoglenoid, similar to the first portion 106 of implant 100. An augment 208 of implant 200 is positioned on the rear of main body 206, and has a second convexity sized and shaped to match or substantially match the concavity of the neoglenoid, similar to second portion 108 of implant 100. The medial surface of the main body 206 in combination with augment 208 creates the complete bone-contacting surface 204. The main body 206 may be formed of a biocompatible polymer, such as polyethylene, and augment 208 may be formed of a biocompatible metal, such as titanium, including porous titanium. As noted above, the polymeric material of the main body 206 may help to provide reduced stiffness of the implant 200, while the metal portions, described in greater detail below, may help provide long-term fixation of the implant 200 to the glenoid.

Augment 208 may be a molded inlay. Thus, main body 206 may be overmolded on augment 208. In other words, the main body 206 may be formed from an injection molding type of process in which the material that will form the main body is placed in a mold (or similar device) in a soft or liquid state and allowed to harden or solidify on the augment 208 to form the desired composite shape. The lateral surface of augment 208 may include a pattern that allows for a better bond or adhesion to the medial surface of main body 206, particularly during the molding process. The pattern may be etched into, engraved into, or built into augment 208, for example in the case of additive manufacturing of the augment 208. The pattern may be a waffle pattern or any other mesh type pattern that may enhance the bond between augment 208 and main body 206.

Augment 208 may include at least one anchor or peg 214 extending from its medial, bone-contacting surface 204. As shown in FIGS. 2A-B, augment 208 may include two anchors 214 extending from its medial, bone-contacting surface 204. Anchors 214 are intended to stabilize the augment against the neoglenoid cortical wall. Anchors 214 may be integral with augment 208 such that augment 208 and pegs 214 are provided as a single piece, for example during additive manufacturing. Thus, anchors 214 may also be formed of biocompatible metal, such as titanium, and may be a porous metal (including porous titanium) to enhance bone ingrowth into augment 208. Anchors 214 may have various shapes. In the illustrated embodiment, anchors include a generally cylindrical body that transitions into a conical or frustoconical tip, but other shapes may be suitable.

One or more pegs or anchors 210, 212 may also extend from the medial or bone-contacting surface 204 of the main body 206. In the illustrated embodiment, these anchors include a center anchor 210 and two peripheral anchors 212, although other numbers and positions of these anchors may be suitable. In the illustrated embodiment, the center anchor 210 and the peripheral anchors 212 have a substantially identical shape, although the center anchor 210 may be slightly larger than the peripheral anchors 212. However, in other embodiments, the center anchor 210 may be a similar size or smaller than one or both peripheral anchors 212, and in some embodiments the center anchor 210 may have a different shape than the peripheral anchors 212.

Figure 2C:
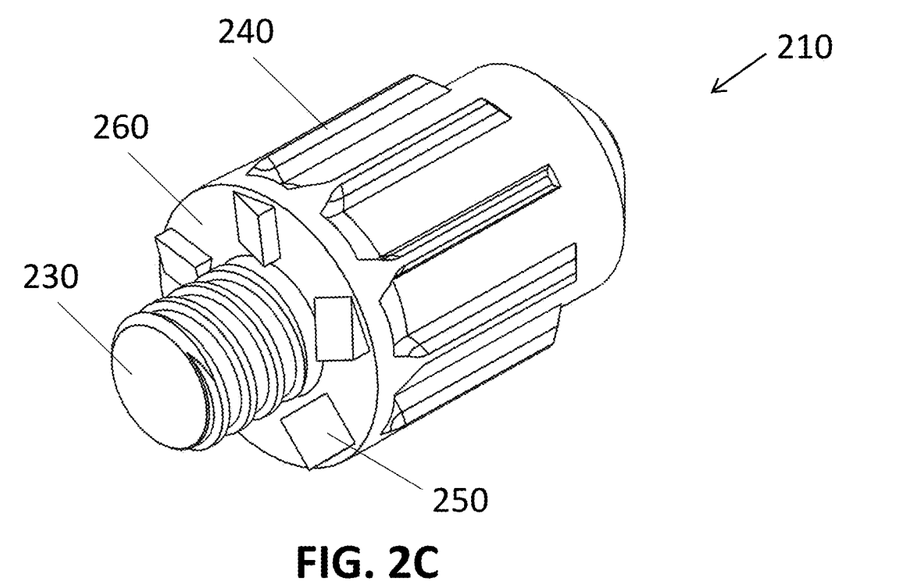
FIGS. 2C-D illustrate perspective views of a center anchor of the augmented implant of FIGS. 2A-B.
Figure 2D:
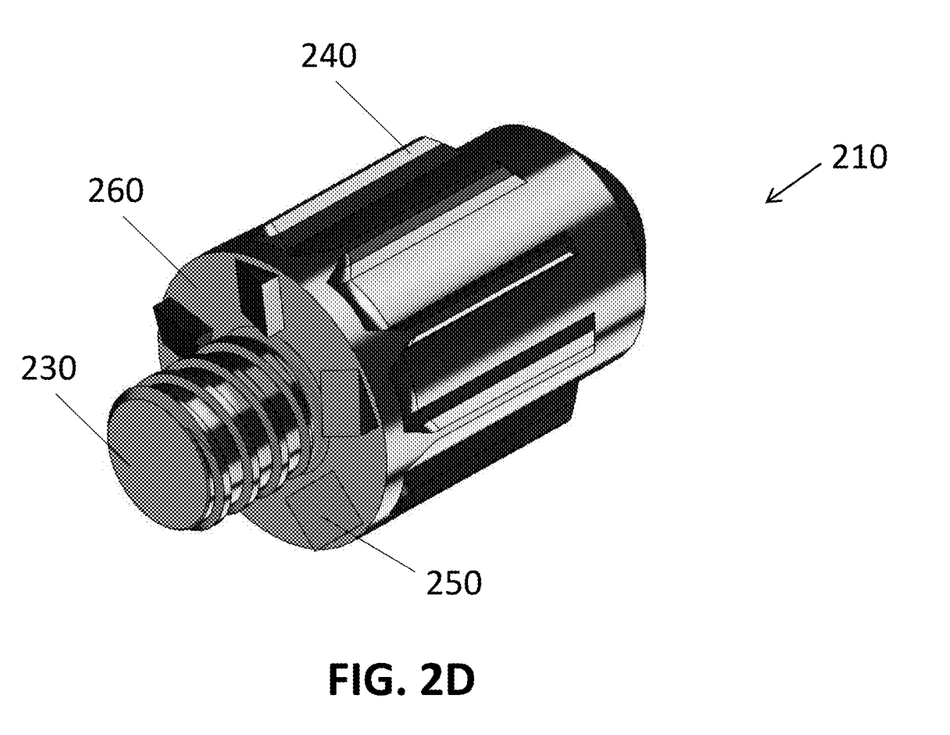

FIGS. 2C-D illustrate perspective views of center anchor 210, although it should be understood that the description of the center anchor 210 may apply similarly or identically to one or both of the peripheral anchors 212. Center anchor 210 may include a base 220 and a body portion. Similarly, peripheral anchors 212 may each include a base 222 and a body portion. Bases 220, 222 may be substantially cylindrical and extend along an axis transverse to the medial, bone-contacting surface 504 of main body 206. The bases 220, 222 may be formed of a polymer, and may be integral with the main body 206. In other words, the main body 206 and bases 220, 222 may be molded as a single monolithic member and formed of a polymer, such as polyethylene, with the rest of main body 206. The body portions of anchors 210, 212 may be generally cylindrical. The body portions of anchors 210, 212 may extend a distance along a longitudinal axis of the anchors 210, 212 before tapering from a first width to a smaller second width, such that the tip portion of the body is conical, frustoconical, or otherwise tapered. However, in some embodiments, the tip portion of the body of anchors 210, 212 may be hemispherical, or have a taper with pointed edges in the shape of a cross or starburst. The body portions of anchors 210, 212 may be formed of a biocompatible metal, such as titanium, and may be a porous metal, including porous titanium, to enhance bone ingrowth into the body portions of the anchors 210, 212.

Center anchor 210 may be located substantially in the center of implant 200, for example a substantially equal distance between the superior and inferior ends of the implant 200, and a substantially equal distance between the anterior and posterior ends of the implant 200. Although FIGS. 2A-B illustrate main body 206 as including two peripheral anchors 212, it may include one peripheral anchor 212, three or more peripheral anchors 212, or in some embodiments, no peripheral anchors 212. Depending on the size of augment 208, the augment 208 may be provided with one or more cutouts or recesses to accommodate the center anchor 210 and/or one or more of the peripheral anchors 212. If augment 208 is relatively small, similar to that shown in FIGS. 1A-B, no cutout or recess may be necessary. If augment 208 is relatively large, similar to that shown in FIGS. 1E-F, cutouts or recesses may be included to accommodate the center anchor 210 and peripheral anchors 212 (and in particular the center base 220 and peripheral bases 222).

Center anchors 210 and peripheral pegs 212 may each be removably coupled to bases 220 and 222, respectively. Center anchor 210 may have a coupling member 230 extending from the body portion of center anchor 210. In one embodiment, the coupling member 230 is a threaded component, and base 220 may have a complementary threaded aperture for receiving the coupling member 230 therein. However, in alternative embodiments, coupling member 230 may have a press fit connection, interference fit, or any other suitable connection mechanism with base 220. The polymeric base 220 of main body 206 may assist in performing a revision procedure to remove implant 200 during a later procedure. For example, compared to metal components that have had bone ingrowth occur, the polymer material may be relatively easily cut away with a tool, such that the base 220 could be relatively easily cut and removed from the metal augment 208 component and the metal body portion of center anchor 210, with the metal portions being more precisely removed from the bone after the polymer portions of implant 200 are cut away. In this scenario, the amount of bone stock that would need to be removed in a revision procedure may be minimized or otherwise reduced. The above description of the coupling member 230 and base 220 of center anchor 210 may apply similarly or identically to the peripheral anchor(s) 212 and corresponding base(s) 222.

Still referring to FIGS. 2A-D, although the center anchor 210 and peripheral anchors 212 are illustrated with male threaded posts while the bases 220, 222 are shown with female threaded sockets, the sockets may instead be provided on the anchors 210, 212 with the posts provided on the bases 220, 222. However, it may be preferable to provide the threaded posts on the anchors 210, 212 and the sockets in the bases 220, 222 as shown. For example, the main body 206 may be molded or otherwise formed from a polymer, with the threaded sockets in the bases 220, 222 being milled with high levels of precision for the positioning of the sockets. Also, the strength of polymers such as polyethylene is typically lower than the strength of metals like titanium. Thus, by providing metal threaded posts in anchors 210, 212 that are inserted into the female polymeric sockets of the bases 220, 222, the assembly may have greater strength than if polymeric threaded posts were provided on the bases 220, 222 with metal female threaded sockets in the anchors 210, 212.

Referring in particular to FIGS. 2C-D, additional features may be provided on center anchor 210, although it should be understood that the same or similar features may also be provided on the peripheral anchors 212. For example, the center anchor 210 may include a plurality of friction-enhancements or texturizations to assist with a user manipulating the center anchor 210. In use, the center anchor 210 may be manually connected to the base 220 via rotation to thread the coupling member 230 into the female socket of the base 220, either by the end user (e.g. a surgeon), by the manufacturer, or by some third party. However, it may be preferable for the manufacturer to couple the center anchor 210 to the base 220, for example to help ensure that appropriate locking torques and assembly forces are uses. With such manual coupling of the center anchor 210 to base 220, gripping features may be helpful. In the illustrated embodiment, a plurality of splines or ridges 240 extend in a longitudinal direction of the center anchor 210, each ridge 240 being spaced apart from another ridge around the circumference of the center anchor 210. The particular number of ridges 240 may be varied as desired, but preferably are numbered and spaced relative to one another to help enhance a user's grip on the center anchor 210, particularly during rotation of the center anchor 210 during coupling to base 220. However, even if the center anchor 210 is not coupled to base 220 via manual rotation, ridges 240 may help a tool to drive the center anchor 210 into base 220. For example, a torque-limiting driver may be engaged with (or adapted to actuate against) the ridges 240 of the center anchor 210 in order to assist with screwing the center anchor 210 into the base 220. In addition, once the center anchor 210 is coupled to base 220, and the implant 200 is implanted into a native glenoid, the ridges 240 may assist in preventing the center anchor 210 from rotation, which could tend to disconnect or loosen the center anchor 210 from the base 220 of implant 200. For example, after insertion of the implant 200 into the bone, the ridges 240 may insert into the bone, with native bone stock being positioned between circumferentially adjacent ridges 240, helping to prevent any further rotation of the center anchor 210, particularly before long term fixation occurs, for example via bone-ingrowth. It should be understood that the ridges 240 may provide additional and/or alternative functionality. For example, the ridges 240 may assist in centering the center anchor 210 into (and/or providing a press-fit with) a hole drilled in the bone to receive the center anchor 210, during and after the center anchor 210 is advanced into the corresponding hole in the bone. In some embodiments, the ridges 240 are formed of a solid metal, such as solid titanium, while the main body of the center anchor 210 is formed of a porous metal, such as porous titanium.

Another additional feature that may be provided on center anchor 210 is wedges 250. Similar or identical wedges may be provided on one or more of the peripheral anchors 212. Still referring to FIGS. 2C-D, center anchor 210 may include a substantially circular base 260 where the main body of the center anchor 210 transitions into connecting member 230, shown in this embodiment is a threaded post. The base 260 of center anchor 210 may be sized and shaped to substantially match the corresponding base 220 in main body 206, so that when the center anchor 210 is screwed into, or otherwise coupled to, the base 220 of the main body 206, the outer surface of the base 220 of the main body 206 is substantially flush with the outer surface of the anchor 210, excluding ridges 240. Wedges 250 may be positioned on base 260 so that, upon coupling of center anchor 210 to the base 220 of main body 206, the wedges 250 confront and eventually contact the base 220 of main body 206. The plurality of wedges 250 may be provided spaced apart from one another around base 260, so that the threaded post or connecting member 230 is positioned radially within the plurality of wedges 250. Each wedge 250 may have a substantially square or rectangular profile, with a first edge of each wedge positioned at the same level or height as base 260, with the opposite second edge positioned at a greater height from the base 260, so that the remaining two sides of wedge 250 have a substantially triangular shape, forming a traditional wedge shape. With this configuration, the second edge of each wedge 250 may form a shoulder or abutment at substantially a right angle with base 260. Each wedge 250 preferably has the same directionality of incline, and the directionality of that incline is preferably oriented so that, as the center anchor 210 is rotated to couple the center anchor 210 to the base 220 of the main body 260, the first edge of the wedges 250 lead in the direction of rotation, while the opposite second edges forming the shoulder or abutment trail in the direction of rotation. With this configuration, as center anchor 210 is coupled to base 220 by rotating the center anchor 210 to thread the connecting member 230 into the corresponding female socket of the base 220, the metal wedges 250 will begin to dig into the polymeric base 220, with the first edge leading the digging motion. Once the center anchor 210 is fully threaded into the base 220 and the base 260 of the center anchor 210 is in contact with the base 220 of the main body 206, the shoulders or abutments defined by the second edges of the wedges 250 provide resistance against unintentional rotation of the center anchor 210 in a direction that would tend to unthread the connecting member 230 from the corresponding female socket of base 220. Thus, the wedges 250 may provide an anti-backout or anti-rotation functionality to help maintain the threads of connecting member 230 secured to the base 220 of the main body 206. In one embodiment, it may be preferable to form the connecting member 230 and/or the plurality of wedges 250 from a solid metal, such as solid titanium. Although wedges 250 are one example of an anti-rotation feature, it should be understood that other anti-rotation features with similar functionality may be suitable. Although the various components of center anchor 210 may be formed from any combination of solid and porous metal (including only porous metal, or only solid metal), in one embodiment, the main body of center anchor 210 is formed of a porous metal, such as porous titanium, while the ridges 240, wedges 250, and connecting member 230 are all formed from a solid metal, such as solid titanium.

It may be difficult or impossible to machine center anchor 210 to have threads on the connecting member 230, wedges 250 on the base 260, and ridges 240 on the main body of center anchor 210 using traditional subtractive manufacturing or casting. The below discussion applies equally to the peripheral anchors 212. For example, because of the small size of the center anchor 210, and the small size and positions of ridges 240, wedges 250, and threads of connecting member 230 (including the existence of small, recessed gap spaces), tools may not effectively be able to access the requires areas to form these features by subtractive manufacturing. This may be especially true for the wedges 250 and the threads of connecting member 230, due to their positions relative to one another. Thus, it is preferable to form center anchor 210 (and peripheral anchors 212) using additive manufacturing, such as 3D printing. As noted above, it is preferable to form the center anchor 210 (and peripheral anchors 212) from a metal, some or all of which is preferably a porous metal such as porous titanium, to enhance bone ingrowth and long-term fixation of implant 200 into the glenoid. In one embodiment, laser rapid manufacturing (LRM) techniques may be used to form the desired geometry of the porous metal, such as porous titanium, forming the center anchor 210. Casting and subtractive manufacturing methods may be unable to provide the desired porous metal ingrowth surfaces.

According to one embodiment, a method of manufacturing prosthetic glenoid implant 200 may include first forming augment 208 having a first convexity adapted to substantially match a neoglenoid surface of a patient's native glenoid. The augment 208 may be formed of metal, including titanium, including porous titanium, via any suitable method, including additive manufacturing. The main body 206 may be overmolded onto the augment 208, and the main body 206 may be formed of a polymer, such as polyethylene. The main body 206 may be molded so that a medial surface includes a second convexity adapted to substantially match a paleoglenoid surface of a patient's native glenoid, and so that a lateral surface has a concavity or other suitable shape adapted to articular with a native or prosthetic humeral head of the patient. The one or more bases 220, 222 may be milled or drilled to form threads therein. However, it should be understood that the bases 220, 222 may be formed with smooth holes, and the central anchor 210 and peripheral anchors 212 may be configured to self-tap into the smooth hole. Before, during, or after forming the augment 208 and/or the main body 206, the center anchor 210 and one or more peripheral anchors 212 may be formed by additive manufacturing, such as 3D printing, preferably using a metal such as titanium, including porous titanium. The manufacturer, an end user, or some third party may couple each of the center anchor 210 and peripheral anchors 212 to the corresponding bases 220, 222 by threading the threaded posts of the anchors into the corresponding threads in the bases, until the wedges of the anchors drive into the bases.

According an embodiment, a method of implanting glenoid implant 200 into a native glenoid of a patient may include first preparing the native glenoid, for example by reaming or otherwise preparing the paleoglenoid surface and the neoglenoid surface for implantation of implant 200. The central anchor 210 and peripheral anchors 212 may be coupled to the main body 206 of implant 200 at any time prior to implanting the glenoid implant 200 on to the glenoid. If desired, one or more holes may be created in the native glenoid to receive any one or more of central anchor 210, peripheral anchors 212, and anchors 214. The glenoid implant 200 may be driven into the native glenoid using any suitable method, including via impaction, to drive the various anchors into the bone. Upon driving central anchor 210 and peripheral anchors 212 into the glenoid, as noted above, ridges 240 may help prevent unintentional rotation of the anchors by friction with the bone, while wedges 250 may help prevent unintentional rotation of the anchors by friction with the polymeric bases 220, 222 of the main body 206 of glenoid implant 200. It should be understood that this method may be performed without using any bone cement or other similar adhesives to couple the glenoid implant 200 to the glenoid. However, bone cement may be used if desired, for example by placing a small amount of bone cement in holes in the glenoid formed to receive the various anchors.

Although glenoid implant 200 is described as including a biconvex medial surface for implantation onto a glenoid with eccentric glenoid erosion, it should be understood that the implant 200 is not so limited. For example, glenoid implant 200 may instead be formed as a glenoid implant for use in a patient without eccentric glenoid erosion, so that the medial bone-contacting surface of the glenoid has substantially only one convexity. In this scenario, the augment 208 and anchors 214 may be omitted, with the entire medial bone-contacting surface of the glenoid implant being formed by the main body. In this scenario, the anchors 214 may be replaced by anchors similar to peripheral anchors 212, and thus the main body of the glenoid implant may include additional bases to receive the additional peripheral anchors.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A glenoid implant system comprising:
    a main body defining an articulating surface configured to articulate with a humeral head, and an opposite bone-contacting surface adapted to contact the glenoid of a patient and defining a periphery of the main body, the main body being formed from a polymer material;
    a base formed in the bone-contacting surface of the main body; and an anchor having a main section and an anti-rotation feature disposed on a base of the anchor, the anti-rotation feature adapted to contact the base formed in the bone-contacting surface of the main body when the anchor is coupled to the base; and an augment portion positioned on the main body, formed separately from the main body, and formed from a metal material, the augment portion having a bone-contacting surface defining a first convexity adapted to contact a neoglenoid portion of the glenoid, the bone-contacting surface of the main body having a second convexity adapted to contact a paleoglenoid portion of the glenoid, the first convexity being different than the second convexity, wherein the main body portion is overmolded on the augment portion, and wherein the bone-contacting surface of augment portion and bone-contacting surface of the main body portion intersect at an interface, the interface extending from a first location at the periphery of the main body to a second location remote from the first location.

2. The glenoid implant system of claim 1, wherein the anchor further includes a threaded post extending from the main section, the threaded post being configured to be received within a hole formed in the base formed in the bone-contacting surface of the main body.

3. The glenoid implant system of claim 2, wherein the anchor includes a plurality of ribs extending in a longitudinal direction of the main section, the plurality of ribs being spaced apart from one another in a circumferential direction of the main section.

4. The glenoid implant system of claim 3, wherein the anti-rotation feature includes a plurality of wedges.

5. The glenoid implant system of claim 4, wherein the anchor is at least partially formed of metal.

6. The glenoid implant system of claim 1, wherein the augment portion includes an augment anchor adapted to engage the neoglenoid portion of the humerus.

7. The glenoid implant system of claim 6, wherein the augment anchor is integral with the augment portion.

8. The glenoid implant system of claim 1, wherein the anchor includes a center anchor and at least one peripheral anchor, and the base formed in the bone-contacting surface of the main body includes a center base and at least one peripheral base, the center base being positioned in a central area of the bone-contacting surface of the main body.

9. The glenoid implant system of claim 4, wherein each of the plurality of wedges includes a first edge extending a first distance from the base of the anchor, and a second edge opposite the first edge extending a second distance from the base of the anchor, the second distance being greater than the first distance.

10. The glenoid implant system of claim 9, wherein each of the plurality of wedges is oriented so that, upon rotation of the anchor in a first direction to couple the anchor to the base, the first edges of the plurality of wedges lead the rotation, and the second edges of the plurality of wedges trail the rotation.

11. The glenoid implant system of claim 10, wherein when the anchor is coupled to the main body so that the base of the anchor is in contact with the base formed in the bone-contacting surface of the main body, the plurality of wedges extend a distance into the main body to prevent rotation of the anchor in a second direction opposite the first direction.

12. The glenoid implant system of claim 1, wherein the anchor is made of a metal material.

13. The glenoid implant system of claim 9, wherein each of the plurality of wedges includes a ramped surface extending between the first and second edges and inclined from the second edge toward the first edge.

14. The glenoid implant system of claim 9, wherein each of the plurality of wedges are integral with the base of the anchor so as to form a monolithic structure.

15. The glenoid implant system of claim 9, wherein the base of the anchor includes a planar surface, the plurality of wedges extending from the planar surface.

16. The glenoid implant system of claim 15, wherein the planar surface extends from a threaded post of the anchor to a periphery of the anchor.

17. The glenoid implant system of claim 16, wherein each of the wedges is positioned between the threaded post and the periphery of the anchor.

18. The glenoid implant system of claim 1, wherein the bone-contacting surface of the main body and the bone-contacting surface of the augment portion meet at an angle transverse to an anterior-posterior axis of the implant.

19. The glenoid implant system of claim 18, wherein the angle is 30 degrees from the anterior-posterior axis.

20. The glenoid implant system of claim 18, wherein the first location is at a posterior edge of the periphery of the main body and the interface extends toward the second location in both a posterior to anterior direction and superior to inferior direction.

* * * * *